(12) United States Patent
Lui et al.

(10) Patent No.: US 6,590,101 B2
(45) Date of Patent: Jul. 8, 2003

(54) PROCESS FOR THE PREPARATION OF FLUOROQUINOLONECARBOXYLIC ACIDS

(75) Inventors: Norbert Lui, Köln (DE); Hans Panskus, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/078,608

(22) Filed: Feb. 19, 2002

(65) Prior Publication Data

US 2002/0120138 A1 Aug. 29, 2002

(30) Foreign Application Priority Data

Feb. 23, 2001 (DE) .......................... 101 08 750

(51) Int. Cl.$^7$ ............... C07D 215/16; C07D 401/00; C07C 63/36
(52) U.S. Cl. ............ 546/156; 544/363; 562/490
(58) Field of Search ........... 546/156; 544/363; 562/490

(56) References Cited

U.S. PATENT DOCUMENTS

| | | | | |
|---|---|---|---|---|
| 4,398,029 A | * | 8/1983 | Irikura et al. | 544/363 |
| 4,544,747 A | * | 10/1985 | Ishikawa et al. | 546/156 |
| 4,599,334 A | * | 7/1986 | Petersen et al. | 514/253 |
| 4,762,844 A | * | 8/1988 | Grohe et al. | 514/312 |
| 5,457,104 A | * | 10/1995 | Bartel et al. | 514/234.5 |
| 5,545,642 A | | 8/1996 | Petersen et al. | 514/312 |
| 5,869,661 A | * | 2/1999 | Ochi et al. | 544/128 |

FOREIGN PATENT DOCUMENTS

| | | |
|---|---|---|
| EP | 0 284 935 | 10/1988 |
| GB | 2 146 638 | 4/1985 |

OTHER PUBLICATIONS

Hradil, Pavel et al: "Cyclization of phenacyl 2–((2,2–di(ethoxycarbonyl)–vinyl)amino)benzoate" Collect. Czech. Chem. Commun., Bd. 63, Nr. 4, 1998, Seiten 520–524, XP001069366 Seite 523; Beispiel 6.

Houben–Weyl: "Methoden der Organischen Chemie, Band VIII, Sauerstofferbindungen III" 1952, George Thieme Verlag, Stuttgart XP002197597 Kapitel 4.III, Herstellujg von Carbonsauren durch Umwandlung von Carbonsaurederivaten, Seiten 418–421 Seite 419, Zeile 13, 14.

Fujita, M. et al: "Pyrroloquinolones and 1–10 pyrazoloquinolones as potential antibacterial agents. Synthesis and antibacterial activity" Eur. J. Med. Chem. Chim. Ther. (EN), Bd. 31, Nr. 12, 1996, Seiten 981–988, XP004071793 Seite 987, Absatz 1; Beispiele 11A–C.

* cited by examiner

Primary Examiner—Alan L. Rotman
Assistant Examiner—Taylor V Oh
(74) Attorney, Agent, or Firm—Godfried R. Akorli; Diderico van Eyl

(57) ABSTRACT

Fluoroquinolonecarboxylic acids can be prepared by hydrolysis of the corresponding $C_1$–$C_4$-alkyl esters with addition of water, acetic acid, and sulfuric acid using a drastically reduced amount of sulfuric acid if, relative to 1 mol of $C_1$–$C_4$-alkyl fluoroquinolonecarboxylate, less than 30 g of sulfuric acid are employed, the reaction mixture is heated to reflux for 0.5 to 8 hours, then a mixture of acetic acid, $C_1$–$C_4$-alkyl acetate, $C_1$–$C_4$-alkyl alcohol, and optionally water is distilled off, and finally the fluoroquinolonecarboxylic acid prepared is isolated.

10 Claims, No Drawings

PROCESS FOR THE PREPARATION OF FLUOROQUINOLONECARBOXYLIC ACIDS

BACKGROUND OF THE INVENTION

The present invention relates to an advantageous process for the preparation of fluoroquinolonecarboxylic acids by acidic hydrolysis of the corresponding fluoroquinolonecarboxylic acid esters.

Fluoroquinolonecarboxylic acids are-important intermediates for the preparation of known pharmaceutically active compounds from the class consisting of the quinolones.
It is known (see EP-A 169,993) that cyclopropyl-6-fluoro-1,4-dihydro-4-oxo-quinolinecarboxylic acid esters can be hydrolyzed under acidic or basic conditions to give the corresponding quinolonecarboxylic acids (loc. cit. page 10, lines 4 to 7). The hydrolysis of-94 g of ethyl 1-cyclopropyl-6,7,8-trifluoro-1,4-dihydroxy-4-oxo-3-quinolinecarboxylate acid with addition of water, glacial acetic acid, and 70 ml (128.8 g) of concentrated sulfuric acid (which corresponds to about 420 g of sulfuric acid per mole of the fluoroquinolonecarboxylic acid ester) is now described in more concrete terms, the reaction mixture being heated under reflux for 1.5 hours, then the suspension present being poured onto ice and then the precipitate that is present being filtered off with suction, washed, and dried (loc. cit. page 28, last paragraph). The yield here is 96% of theory.

A disadvantage of this process is the large amount of sulfuric acid that is needed, the large amounts of waste water and the disposal problems thus resulting, which result from the use of large amounts of sulfuric acid (which is then obtained as dilute acid) and ice, and the necessity to wash the isolated product a number of times in order to remove adhering sulfuric acid residues.

SUMMARY OF THE INVENTION

There has now been found a process for the preparation of fluoroquinolonecarboxylic acids by hydrolysis of the corresponding $C_1$–$C_4$-alkyl esters comprising
(a) mixing water, acetic acid, and sulfuric acid with a $C_1$–$C_4$-alkyl fluoroquinolonecarboxylate, wherein less than 30 g of sulfuric acid per 1 mol of $C_1$–$C_4$-alkyl fluoroquinolonecarboxylate are employed,
(b) heating the resultant reaction mixture at reflux for 0.5 to 8 hours,
(c) distilling off a mixture of acetic acid, $C_1$–$C_4$-alkyl acetate, $C_1$–$C_4$-alkyl alcohol, and optionally water, and
(d) isolating the resultant fluoroquinolonecarboxylic acid.

DETAILED DESCRIPTION OF THE INVENTION

Suitable $C_1$–$C_4$-alkyl fluoroquinolonecarboxylates to be employed are, for example, those of the formula (I)

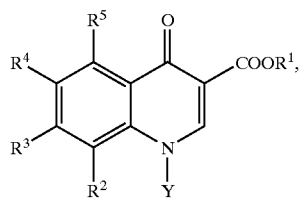

(I)

in which $R^1$ represents $C_1$–$C_4$-alkyl,
$R^2$ represents hydrogen, $C_1$–$C_4$-alkyl, $C_1$–$C_4$-alkoxy, halogen, nitro, or cyano,
$R^3$ and $R^4$ each represent halogen,
$R^5$ represents hydrogen, $C_1$–$C_4$-alkyl, halogen, or nitro, and
Y represents $C_1$–$C_6$-alkyl, cyclopropyl, or phenyl, each of which is optionally substituted by halogen, or $R^2$ and Y together represent a —$CH_2$—$CH_2$—O— or—-CH($CH_3$)—$CH_2$—O— bridge bonded to the quinolone ring nitrogen atom by a carbon atom,
with the proviso that at least one of the radicals $R^2$ to $R^5$ represents fluorine.

Starting from the $C_1$–$C_4$-alkyl fluoroquinolonecarboxylates of the formula (I), for example, it is possible to obtain the corresponding fluoroquinolonecarboxylic acids of the formula (II)

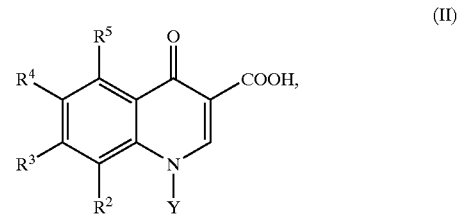

(II)

in which the radicals $R^2$ to $R^5$ and Y have the meaning indicated for formula (I).

Preferably, in the formulas (I) and (II),
$R^2$ represents hydrogen, methyl, methoxy, fluorine, chlorine, nitro, or cyano,
$R^3$ represents fluorine or chlorine,
$R^4$ represents fluorine,
$R^5$ represents hydrogen, methyl, fluorine, chlorine, or nitro, and
Y represents methyl, ethyl, isopropyl, cyclopropyl, fluorocyclopropyl, 4-fluorophenyl, or 2,4-difluorophenyl.

Preferably, in formula (I) $R^1$ represents methyl or ethyl.

In the process according to the invention, acetic acid and sulfuric acid can be employed in water-containing or anhydrous form. The quantitative data described relate to 100% strength acetic acid and 100% strength sulfuric acid. If water-containing acetic acid and/or water-containing sulfuric acid is employed, less water must be employed according to their water content. Acetic acid is preferably employed in the form of glacial acetic acid, and sulfuric acid is preferably employed in the form of 96 to 100% strength sulfuric acid.

Relative to 1 mol of $C_1$–$C_4$-alkyl fluoroquinolonecarboxylate, it is possible to employ in the process according to the invention, for example, 20 to 250 ml of water, 200 to 2000 ml of acetic acid, and 2 to 25 g of sulfuric acid. Preferably, the amounts are 100 to 200 ml of water, 300 to 1000 ml of acetic acid, and 3 to 15 g of sulfuric acid.

The addition of water, acetic acid, and sulfuric acid is preferably carried out such that the $C_1$–$C_4$-alkyl fluoroquinolonecarboxylate, the water, and the acetic acid are introduced before the sulfuric acid is added.

The reaction mixture is preferably heated to reflux for 1 to 5 hours.

After completion of the heating to reflux, acetic acid, $C_1$–$C_4$-alkyl acetate, $C_1$–$C_4$-alkyl alcohol, and water are distilled off from the reaction mixture. The distillation can be conducted, for example, until a bottom temperature in the range from 107 to 113° C. results. The distillation is preferably conducted until a bottom temperature in the range from 108 to 110° C. results. These temperatures relate to normal pressure. If the reaction is carried out at other pressures, these temperatures are to be set correspondingly lower or higher.

The 3 to 4 components distilling off in the distillation distil, inter alia, in the form of azeotropes for which the composition can change during the distillation.

The heating of the reaction mixture to reflux and the subsequent distillation can be carried out at reduced pressure, atmospheric pressure, or elevated pressure. For example, pressures in the range from 0.5 to 3 bar are possible. Preferably, both process steps are carried out at atmospheric pressure.

The fluoroquinolonecarboxylic acid prepared from the mixture present after the distillation can be isolated, for example, by diluting this mixture with water and filtering off the precipitate then present with suction, washing the precipitate with water, and drying it. It is advantageous to wash the isolated product a number of times in order to obtain it sufficiently free and largely without adhering sulfuric acid.

Preferably, the isolation of the fluoroquinolonecarboxylic acid prepared is carried out by setting a pH in the range from 2 to 5 (preferably 3 to 4) in the mixture that is present after the distillation by addition of a base. This can be achieved, for example, by adding an appropriate amount of sodium hydroxide solution or sodium acetate. Preferably, a 1 to 20% strength by weight aqueous sodium acetate solution is used. The pH optimal for the isolation of a specific fluoroquinolonecarboxylic acid can be determined by a simple titration. The pH resulting from the titration is therefore chosen on the one hand to be as high as possible but on the other hand not so high as to lead to the precipitation of the salts of the respective fluoroquinolonecarboxylic acid. After setting the pH, the mixture can be cooled, for example, to 0 to 35° C., and the precipitate then present can be filtered off, washed with water, and dried. The drying is preferably carried out at elevated temperature and reduced pressure. As a rule, an adequately pure product can be obtained even with a single washing.

Using the process according to the invention, fluoroquinolonecarboxylic acids are in general obtained in yields of 98% of theory and higher.

In the manner according to the invention, it is particularly possible to obtain the following fluoroquinolonecarboxylic acids in an advantageous manner: 1-cyclopropyl-6,7,8-trifluoro-1,4-dihydro-4-oxo-3-quinolinecarboxylic acid, 1-cyclopropyl-6,7-difluoro-1,4-dihydro-4-oxo-3-quinoline carboxylic acid, 1-cyclopropyl-6,7-difluoro-8-cyano-1,4-dihydro-4-oxo-3-quinolinecarboxylic acid, 1-(2-fluoro) cyclopropyl-6,7-difluoro-1,4-dihydro-4-oxo-3-quinolinecarboxylic acid, 1-cyclopropyl-8-chloro-6,7-difluoro-1,4-dihydro-4-oxo-3-quinolinecarboxylic acid, and 1-ethyl-6,7,8-trifluoro-1,4-dihydro-4-oxo-3-quinolinecarboxylic acid.

The process according to the invention has the advantage that, compared with the prior art, very much less sulfuric acid (only about 1 to 10% of the amount previously used) is employed and therefore the amount of dilute acid formed is significantly lower. If the advantageous, pH-controlled method for the isolation of the fluoroquinolonecarboxylic acids that is prepared is also used, washing operations can be avoided and further reductions in the amount of waste water realized. Finally, the yield of desired product is higher than previously obtained.

The advantages resulting according to the invention are very surprising, since if only the amount of sulfuric acid is reduced compared with the prior art but the distillation is not carried out or if the amount of sulfuric acid is reduced and the mixture is only briefly heated to reflux, then the hydrolysis no longer proceeds almost quantitatively but instead proceeds only incompletely, which leads to reductions in yield and product impurities (see comparison examples).

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

300 g of ethyl 1-cyclopropyl-6,7,8-trifluoro-1,4-dihydro-4-oxo-3-quinolinecarboxylate, 106.8 g of water, and 426 g of acetic acid were introduced and 3.8 g of sulfuric acid were added. The mixture was heated at reflux for 3 hours. 310 ml of distillate were then distilled off until a bottom temperature of 109° C. was reached. The mixture was then cooled to 80° C. and 157.5 g of 4.8% strength by weight sodium acetate solution were added dropwise. The pH was then in the range 3 to 4. The mixture was then cooled to 20° C. and the solid was filtered off with suction. The solid was washed with 200 ml of water and dried in vacuo at 50° C. 270.3 g of 1-cyclopropyl-6,7,8-trifluoro-1,4-dihydro-4-oxo-3-quinolinecarboxylic acid were isolated, which corresponds to a yield of 99% of theory.

Example 2

1500 g of ethyl 1-cyclopropyl-6,7-difluoro-1,4-dihydro-4-oxo-3-quinolinecarboxylate, 128.4 g of water, and 4500 g of acetic acid were introduced and 53 g of sulfuric acid were added. The mixture was heated at reflux for 4 hours. 2020 ml of distillate were then distilled off until a bottom temperature of 109° C. was reached. The suspension was then cooled to 80° C. and 2204 g of 4% strength by weight sodium acetate solution were added dropwise. The pH was then in the range 3 to 4. The mixture was then cooled to 20° C. and the solid was filtered off with suction. The solid was washed with 2000 ml of water and dried in vacuo at 50° C. 1329 g of 1-cyclopropyl-6,7-difluoro-1,4-dihydro-4-oxo-3-quinolinecarboxylic acid were isolated, which corresponds to a yield of 98%.

Comparison Example 1

300 g of ethyl 1-cyclopropyl-6,7,8-trifluoro-1,4-dihydro-4-oxo-3-quinolinecarboxylate, 106.8 g of water, and 426 g of acetic acid were introduced and 3.8 g of sulfuric acid were added. The mixture was heated to reflux and 310 ml of distillate were immediately distilled off. The suspension was cooled to 80° C. and 157.5 g of 4.8% strength aqueous sodium acetate solution were added dropwise. The reaction mixture was then cooled to 20° C. and the solid was filtered off with suction. The solid was washed with 200 ml of water and dried in vacuo at 50° C. The solid consisted of a mixture of ethyl 1-cyclopropyl-6,7,8-trifluoro-1,4-dihydro-4-oxo-3-quinolinecarboxylate (8%) and 1-cyclopropyl-6,7,8-trifluoro-1,4-dihydro-4-oxo-3-quinolinecarboxylic acid (92%).

This comparison example shows that the use of a small amount of sulfuric acid and only brief heating to reflux affords poorer yields than the prior art.

Comparison Example 2

300 g of ethyl 1-cyclopropyl-6,7,8-trifluoro-1,4-dihydro-4-oxo-3-quinolinecarboxylate, 106.8 g of water, and 426 g of acetic acid were introduced and 3.8 g of sulfuric acid were added. The mixture was heated to reflux for 1.5 hours, then cooled to 80° C., after which 157.5 g of 4.8% strength aqueous sodium acetate solution were added dropwise. The reaction mixture was then cooled to 20° C. and the solid was filtered off with suction. The solid was washed with 200 ml of water and dried in vacuo at 50° C. The solid consisted of a mixture of ethyl 1-cyclopropyl-6,7,8-trifluoro-1,4-dihydro-4-oxo-3-quinolinecarboxylate (11%) and 1-cyclopropyl-6,7,8-trifluoro-1,4-dihydro-4-oxo-3-quinolinecarboxylic acid (89%).

This comparison example shows that the use of a small amount of sulfuric acid without the distillation that is to be carried out according to the invention affords poorer yields than the prior art.

What is claimed is:

1. A process for the preparation of fluoroquinolonecarboxylic acids by hydrolysis of the corresponding $C_1$–$C_4$-alkyl esters comprising
   (a) mixing water, acetic acid, and sulfuric acid with a $C_1$–$C_4$-alkyl fluoroquinolonecarboxylate, wherein less than 30 g of sulfuric acid per 1 mol of $C_1$–$C_4$-alkyl fluoroquinolonecarboxylate are employed,
   (b) heating the resultant reaction mixture at reflux for 0.5 to 8 hours,
   (c) distilling off a mixture of acetic acid, $C_1$–$C_4$-alkyl acetate, $C_1$–$C_4$-alkyl alcohol, and optionally water, and
   (d) isolating the resultant fluoroquinolonecarboxylic acid.

2. A process according to claim 1 wherein a $C_1$–$C_4$-alkyl fluoroquinolonecarboxylate of the formula

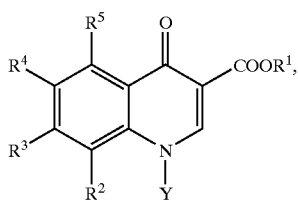

(I)

in which
   $R^1$ represents $C_1$–$C_4$-alkyl,
   $R^2$ represents hydrogen, $C_1$–$C_4$-alkyl, $C_1$–$C_4$-alkoxy, halogen, nitro, or cyano,
   $R^3$ and $R^4$ each represent halogen,
   $R^5$ represents hydrogen, $C_1$–$C_4$-alkyl, halogen, or nitro, and
   Y represents $C_1$–$C_6$-alkyl, cyclopropyl, or phenyl, each of which is optionally substituted by halogen, or $R^2$ and Y together represent a —CH$_2$—CH$_2$—O— or —CH(CH$_3$)—CH$_2$—O— bridge bonded to the quinolone ring nitrogen atom by a carbon atom,
with the proviso that at least one of the radicals $R^2$ to $R^5$ represents fluorine, is hydrolyzed to form a fluoroquinolonecarboxylic acid of the formula

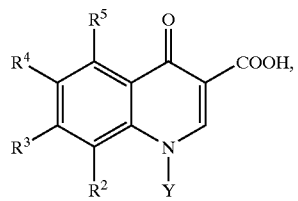

(II)

in which the radicals $R^2$ to $R^5$ and Y have the meaning indicated for formula (I).

3. A process according to claim 2 wherein
   $R^1$ represents methyl or ethyl,
   $R^2$ represents hydrogen, methyl, methoxy, fluorine, chlorine, nitro, or cyano,
   $R^3$ represents fluorine or chlorine,
   $R^4$ represents fluorine,
   $R^5$ represents hydrogen, methyl, fluorine, chlorine, or nitro, and
   Y represents methyl, ethyl, isopropyl, cyclopropyl, fluorocyclopropyl, 4-fluorophenyl, or 2,4-difluorophenyl.

4. A process according to claim 1 wherein 1-cyclopropyl-6,7,8-trifluoro-1,4-dihydro-4-oxo-3-quinolinecarboxylic acid, 1-cyclopropyl-6,7-difluoro-1,4-dihydro-4-oxo-3-quinolinecarboxylic acid, 1-cyclopropyl-6,7-difluoro-8-cyano-1,4-dihydro-4-oxo-3-quinolinecarboxylic acid, 1-(2-fluoro)cyclopropyl-6,7-difluoro-1,4-dihydro-4-oxo-3-quinolinecarboxylic acid, 1-cyclopropyl-8-chloro-6,7-difluoro-1,4-dihydro-4-oxo-3-quinolinecarboxylic acid, or 1-ethyl-6,7,8-trifluoro1,4-dihydro-4-oxo-3-quinolinecarboxylic acid is prepared.

5. A process according to claim 1 wherein, relative to 1 mol of $C_1$–$C_4$-alkyl fluoroquinolonecarboxylate, 20 to 250 ml of water, 200 to 2000 ml of acetic acid, and 2 to 25 g of sulfuric acid are employed, wherein the amount of acetic acid is calculated based on 100% strength acetic acid and the amount of sulfuric acid is calculated based on 100% strength sulfuric acid.

6. A process according to claim 1 wherein the acetic acid is employed in the form of glacial acetic acid and the sulfuric acid is employed in the form of 96 to 100% strength sulfuric acid.

7. A process according to claim 1 wherein the distillation is conducted until reaching a bottom temperature in the range from 107 to 113° C. at a pressure of one atmosphere.

8. A process according to claim 1 wherein the fluoroquinolonecarboxylic acid is isolated at a pH in the range 2 to 5.

9. A process according to claim 8 wherein the pH is set using a 1 to 20% strength by weight aqueous sodium acetate solution.

10. A process according to claim 8 wherein after the pH is set to 0 to 35° C., the mixture is cooled and the precipitate then present is filtered off, washed with water, and dried.

* * * * *